United States Patent [19]

Bush

[11] Patent Number: 4,566,984

[45] Date of Patent: Jan. 28, 1986

[54] ETHER POLYCARBOXYLATES

[75] Inventor: Rodney D. Bush, Cincinnati, Ohio

[73] Assignee: The Procter & Gamble Company, Cincinnati, Ohio

[21] Appl. No.: 672,302

[22] Filed: Nov. 16, 1984

[51] Int. Cl.$^4$ .................. C07C 59/22; C07C 69/66
[52] U.S. Cl. .................. 252/140; 252/89.1; 252/142; 252/144; 562/583; 549/420
[58] Field of Search ............ 252/89.1, 90, 345; 260/535 P, 345.8 R; 562/583; 560/180

[56] References Cited

U.S. PATENT DOCUMENTS

| | | | |
|---|---|---|---|
| 3,293,176 | 12/1966 | White | 210/58 |
| 3,692,685 | 9/1972 | Lamberti et al. | 252/89 |
| 3,835,163 | 9/1974 | Rapko | 260/347.3 |
| 3,923,679 | 12/1975 | Rapko | 252/89 |
| 3,935,257 | 1/1976 | Ruest et al. | 260/535 P |
| 3,950,388 | 4/1976 | Lannert | 260/468 X |
| 3,972,922 | 8/1976 | Harken et al. | 260/535 P |
| 4,102,903 | 7/1978 | Crutchfield et al. | 260/345.7 |
| 4,120,874 | 10/1978 | Crutchfield et al. | 260/345.8 |
| 4,158,635 | 6/1979 | Crutchfield et al. | 252/99 |
| 4,228,300 | 10/1980 | Lannert | 560/180 |
| 4,382,871 | 5/1983 | Lamberti et al. | 252/174.19 |

OTHER PUBLICATIONS

Organic Builders: A Review of Worldwide Efforts to Find Organic Replacements for Detergent Phosphates, M.M. Crutchfield, J. Am. Chemists' Soc., January 1978 (Vol. 55).

Primary Examiner—Paul Lieberman
Assistant Examiner—John F. McNally
Attorney, Agent, or Firm—Edmund F. Gebhardt; Steven J. Goldstein; Jack D. Schaeffer

[57] ABSTRACT

Novel ether carboxylates prepared from ketomalonate esters and diene compounds are disclosed. Detergent compositions incorporating the ether carboxylates can be prepared without use of phosphorus-containing detergent builder materials.

8 Claims, No Drawings

ETHER POLYCARBOXYLATES

TECHNICAL FIELD

The present invention relates to new ether polycarboxylate compounds which are effective sequestering agents and useful in detergent compositions for household, institutional and industrial use.

BACKGROUND ART

The role of sequestering agents in softening water by complexing the "hardness" cations in water supplies is well known. Sequestering agents are recognized aids in detergent processes because they form a soluble complex with calcium and magnesium ions which can react with soaps and other anionic surfactants and otherwise adversely affect detergency. Polyphosphates such as tripolyphosphates and pyrophosphates are widely used as ingredients in detergent compositions in part because of their property of sequestering hardness ions. Such phosphorus-containing compounds as well as nitrogen containing compounds, e.g., nitrilotriacetates, are highly effective. However, the effect of the phosphorus content and the nitrogen content of these sequestering agents upon eutrophication of lakes and streams has been questioned and the use of phosphates in detergent compositions has been subject to government regulation or prohibition.

These circumstances have developed a need for highly effective and efficient phosphorus-free and nitrogen-free sequestering agents and detergency builders.

The object of the present invention is to provide such a class of compounds which are useful as sequestering agents, especially when used as builders in detergent compositions containing surfactants.

U.S. Pat. No. 3,293,176, issued Dec. 20, 1966, to White, discloses ether chelating compounds having carboxylic acid, phosphoric acid or sulfonic acids groups.

U.S. Pat. No. 3,692,685, issued Sept. 19, 1972 to Lamberti et al., discloses detergent compositions containing an ether polycarboxylate having the formula:

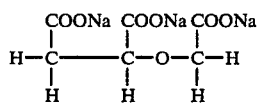

U.S. Pat. No. 4,228,300, issued Oct. 14, 1980, to Lannert, discloses ether polycarboxylate sequestering agents and detergency builders having the formula

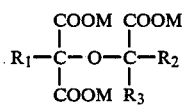

wherein M is alkali metal or ammonium, $R_1$ and $R_2$ are hydrogen, methyl or ethyl and $R_3$ is hydrogen, methyl, ethyl or COOM.

U.S. Pat. Nos. 3,923,679, issued Dec. 2, 1975, and 3,835,163, issued Sept. 10, 1974, both to Rapko, disclose 5-membered ring ether carboxylates. U.S. Pat. Nos. 4,158,635 issued June 19, 1979; 4,120,874, issued Oct. 17, 1978, and 4,102,903, issued July 25, 1978, all to Crutchfield et al. diclose 6-membered ring ether carboxylates.

It is a purpose of the present invention to provide new and superior ether polycarboxylate sequestering agents, detergent compositions containing said sequestering agents and a method for making said sequestering agents.

SUMMARY OF THE INVENTION

The invention comprises metal sequestering agent compounds represented by the chemical structure

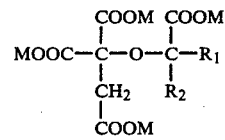

wherein M is hydrogen or a cation wherein the resultant salt is water soluble and $R_1$ and $R_2$ can be the same or different and are selected from the group consisting of hydrogen, methyl, ethyl, hydroxy, hydroxymethyl, hydroxyethyl, carboxy, carboxymethyl and carboxyethyl.

Included in this chemical structure are the compound 3,3-dicarboxy-4-oxa-1,6-hexanedioic acid, water-soluble salts thereof and hydrates thereof.

Another aspect of the invention is detergent compositions containing from about 0.5% to about 98%, preferably from about 5% to about 30%, of a surfactant and from about 2% to about 99.5%, preferably from about 4% to about 50% of one of the metal sequestering agent compounds defined hereinbefore.

Yet another aspect of the invention is a method of making compounds represented by the formula

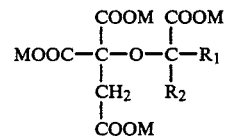

wherein M is hydrogen or a cation wherein the resultant salt is water soluble and $R_1$ and $R_2$ can be the same or different and are selected from the group consisting of hydrogen, methyl, ethyl, hydroxy, hydroxymethyl, hydroxyethyl, carboxy, carboxymethyl and carboxyethyl or $R_2$ can be a methylene or ethylene link to the specified methylene carbon replacing one hydrogen atom to form a 5- or 6-membered saturated ring.

The method comprises reacting a conjugated diene compound with a dialkyl ketomalonate followed by hydrolysis of the resulting diester to a dicarboxylate and oxidation to an ether carboxylate compound containing a total of at least four carboxylate groups.

DETAILED DESCRIPTION OF THE INVENTION

The following example is illustrative of a synthesis for preparing 3,3-dicarboxy-4-oxa-1,6-hexanedioic acid, tetrasodium salt.

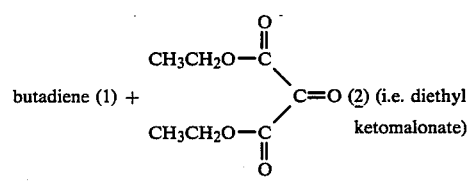

-continued to yield

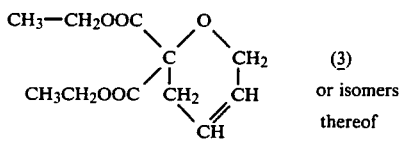 (3) or isomers thereof which is reacted with an alkali metal hydroxide to yield

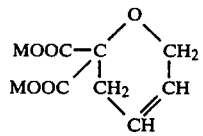 (4)

which is oxidized and neutralized to yield

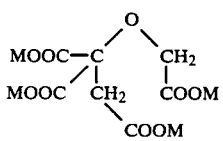 (5)

or hydrates thereof wherein M is sodium or potassium.

Formation of 3

250 ml. of 1,3-butadiene (Matheson, G. P. grade, 99.0% pure) was condensed into a graduated cylinder containing 0.5 g. calcium hydride under anhydrous conditions. This material was then added to a glass autoclave liner which was cooled with dry ice and contained 200 ml. of acetonitrile, 0.5 g. hydroquinone and 0.1 g. of calcium hydride. The resulting solution was then combined with 250 grams of 2/2 and placed in the autoclave and pressurized to 600 lbs./in. using nitrogen and then heated to 155° C. for at least 16 hours. After cooling, the reaction mixture was transferred to a rounded-bottom flask and the volatiles removed by aspiration. The resulting liquid was then distilled under vacuum to give three fractions:

(1) b.p. 20°-50° C. at 0.1 mm, 20 g of mostly 2
(2) b.p. 40°-90° C. at 0.1 mm, 30 g, 50:50 2 & 3
(3) b.p. 90°-105° C. at 0.1 mm, 250 g 3

3 was characterized by NMR ('H and $^{13}$C) and IR spectroscopy.

Formation of 4

A solution consisting of 640 ml. water and 56.2 g. (1.4 mole) sodium hydroxide was placed in a 2 liter, 3-necked flask equipped with a condenser, mechanical stirrer and positive nitrogen. The solution was then heated to 90° C. and 160 g. (0.702 mole) of 3 was added. A exothermic reaction was noted. The resulting mixture was stirred for 30 minutes and allowed to cool to room temperature. The resulting solution of 4 could be stored at 0° C. and used for the formation of 5.

Formation of 5

80 g. (0.37 mole) of 4 (as a solution in water from the previous step) was placed in a glass reactor along with 62.9 g. (0.55 mole) of 30% hydrogen peroxide. Then this solution was cooled in an ice-bath while 0.37 mole of ozone was bubbled into the reaction solution in a stream of oxygen. Sodium hydroxide was added until the pH remained at 9.5 for at least 24 hours. This usually took 50-60 ml. of 25% sodium hydroxide and about 72 hours. The solution was then evaporated and dried by vacuum at 80° C. to give a solid (usually white) which was characterized by $^{13}$C and 'H NMR and elemental analysis (mass spectral analysis of the corresponding tetramethyl ester) as compound 5. 5 was usually obtained as the trihydrate.

Compounds of the invention other than 3,3-dicarboxy-4-oxa-1,6-hexanedioic acid, tetrasodium salt, can be prepared by substitution of appropriate conjugated dienes for 1,3-butadiene. For example, compounds with the formula $CH_2=CH-CH=CR_1R_2$, wherein $R_1$ and $R_2$ are hydrogen, methyl, ethyl, hydroxy, hydroxymethyl, hydroxyethyl, carboxy, carboxymethyl or carboxyethyl and both $R_1$ and $R_2$ are not hydrogen, will react with a dialkyl ketomalonate to produce intermediates that can be hydrolyzed, oxidized and neutralized into compounds of the invention. It is recognized that a random Diels-Alder type of reaction results in a mixture of compounds, but such mixtures are useful as detergency builders in the detergent compositions of the invention.

The cyclic ether polycarboxylate compounds in acid form

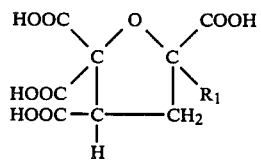 (6)

and

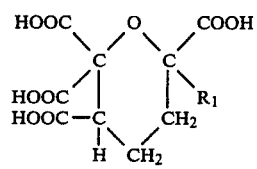 (7)

wherein $R_1$ is hydrogen are prepared by the substitution of 1,3-cyclohexadiene and 1,3-cyclopentadiene respectively for 1,3-butadiene in the reaction scheme disclosed hereinbefore.

In the preparation of compounds 6 and 7 the initial intermediate compounds corresponding to compound 3 are respectively:

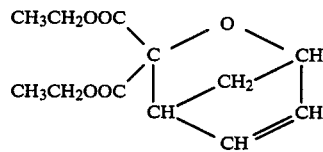 (8)

and

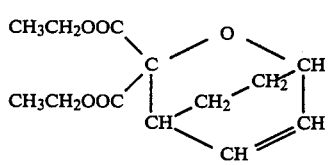 (9)

Hydrolysis of these esters to carboxylate and the oxidization/neutralization step proceed as described in Formation of 4 and Formation of 5 above.

Additional compounds in acid form which can be prepared by the general method include:

3,3,5-tricarboxy-4-oxa-1,6-hexanedioic acid
3,3-dicarboxy-4-oxa-5-hydroxy-1,6-hexanedioic acid
3,3,5-tricarboxy-4-oxa-5-hydroxymethyl-1,6-hexanedioic acid
3,3-dicarboxy-4-oxa-5-hydroxyethyl-1,6-hexanedioic acid Dimethyl ketomalonate and other dialkyl ketomalonates can be substituted for the diethyl ketomalonate of the examples.

Calcium Binding Constants Determination

A computer system (Hewlett-Packard) with digital voltmeters was used to collect and analyze data from an Orion calcium selective electrode and a linear syringe buret (Sage Instruments syringe pump plus a linear potentiometer). An Analog Devices 40J non-inverting operational amplifier electrometer amplified the calcium electrode voltage and provided Nernstian behavior of the electrode into the $10^{-7}$M range. Volumetric accuracy was better than +/− 0.5%.

Three hundred data pairs of [Ca total] vs $10^{(E/S)}$, which is a linear measure of [Ca free], were collected and corrected for dilution during each titration. S is the Nernst equation slope, ca. 29 mv/decade, and E is the calcium electrode voltage. Calcium ion was titrated into buffer solution. Here, L represents the sequestering ligand. A ligand-free standard titration calibrated the electrode response. A second titration, containing a fixed concentration of total ligand [L tot] allowed calculation of $K_{Ca}$ at various [Ca tot]/[L tot] ratios. A third titration, adding Ca ion to a solution of a fixed [L tot] and fixed [Mg tot] was compared with $K_{Ca}$ at different [Ca tot]/[L tot] ratios to reveal $K_{Mg}$ at those same ratios.

$$\text{Run 2: } K_{Ca} = \frac{[\text{Ca tot}] - [\text{Ca free}]}{[\text{Ca free}] \times [\text{L free}]}$$

where [L free] = [L tot] − [Ca tot] + [Ca free]

$$\text{Run 3: } K_{Mg} \text{ in presence of Ca} = \frac{[\text{Mg L}]}{[\text{Mg free}] \times [\text{L free}]}$$

where
[Mg L] = [L tot] − [Ca L] − [L free]
[Mg free] = [Mg tot] − [Mg L]

$$[\text{L free}] = \frac{[\text{Ca L}]}{[\text{Ca free}] \times K_{Ca}}$$

and
[Ca L] = [Ca tot] − [Ca free]

At high ratios of [Ca tot]/[L tot], the polymer became saturated with Ca ion and a linear increase in [Ca free] resulted. This line was extrapolated back to [Ca free]=0 and [Ca tot] at that point represented a measure of calcium binding capacity.

pH was always 9.55, temperature 22° C. Ionic strength ca. 0.1M, [Ca tot]=0 to 1.4 mM (0 to 8.2 gr/gal), [Ligand total]=3.52×$10^{-4}$M, [Mg total]=2.0 mM.

| Calcium Ion Binding Constants (35° C., 0.1 M ionic strength) | Log $K_{Ca}$ | |
|---|---|---|
| | pH 9.5 | pH 7.6 |
| 3,3-dicarboxy-4-oxa-1,6 hexanedioic acid, tetrasodium salt (DCOH) (Compound 5) | 5.5 | 5.3 |
| Oxacyclohexane-2,2,3,6-tetracarboxylic acid, tetrasodium salt (OCHTC) (Compound 7) | 6.2 | — |
| Nitrilotriacetic acid, sodium salt | 5.5 | 3.3 |
| 2-oxa-1,1,3 propanetricarboxylic acid, sodium salt | 4.3 | 4.6 |
| 2-oxa-1,3,4 butanetricarboxylic acid, sodium salt | 4.4 | — |
| Sodium tripolyphosphate | 4.9 | 3.1 |
| Sodium citrate | 3.5 | 2.6 |

These results demonstrate a clear advantage in calcium binding for a compound of the invention, DCOH, and a compound prepared by the process of the invention, OCHTC, relative to two prior art ether carboxylates and sodium citrate, another nonpolymeric carboxylate sequestering agent used as a detergent builder material. DCOH and OCHTC are at least equivalent to sodium tripolyphosphate and sodium nitrilotriacetate in calcium binding, while being nitrogen and phosphorus-free.

The results indicate that the polycarboxylates of the present invention are superior sequestering agents compared to other ether carboxylates previously disclosed in the art.

Detergent Compositions

Detergent compositions incorporating the sequestering agents of the present invention contain as essential components from about 0.5% to about 98% of a surfactant and from about 2% to about 99.5% of a sequestering agent compound of the present invention as a detergency builder.

Typical laundry detergent compositions within the scope of the present invention contain from about 5% to about 30% of a surfactant and from about 10% to about 80% total detergency builder, of which from about 20% to 100% by weight of total detergency builder can be the sequestering agents of the present invention.

The compositions of this invention are effective over the broad pH range of about 6 to 12. The compositions can be formulated to provide a desired pH in the ranges by proper selection of appropriate salts. Thus, for example, preferred water-soluble salts for both the detergent and sequestering agent, are alkali metal salts such as sodium, potassium, lithium and ammonium or alkyl-substituted ammonium, e.g. triethanol ammonium. Sodium and potassium are preferred water-soluble cations.

Depending on the pH of the desired solution, the salts are partially or fully neutralized.

The detergent compositions can be prepared as solid (granular, tablet, powder) or liquid (aqueous or non-aqueous-based) physical forms.

The detergent compositions of the invention are particularly suitable for laundry use, but are also suitable for the cleaning of hard surfaces and for dishwashing. Detergent compositions formulated for use in automatic dishwashing machines typically contain from about 0.5% to about 6% of a low sudsing nonionic surfactant, from about 40% to about 99% of a mixture of detergency builder materials and a component that provides hypochlorite ions in water solution.

Various types of surfactants can be used in conjunction with the novel sequestering agents of this invention. Useful surfactants include anionic, nonionic, ampholytic, zwitterionic and cationic surfactants or mixtures of such materials.

(A) Anionic soap and non-soap surfactants

This class of surfactants includes ordinary alkali metal monocarboxylates (soaps) such as the sodium, potassium, ammonium and alkylolammonium salts of higher fatty acids containing from about 8 to about 24 carbon atoms and preferably from about 12 to about 18 carbon atoms. Suitable fatty acids can be obtained from natural sources such as, for instance, from plant or animal esters (e.g., palm oil, coconut oil, babassu oil, soybean oil, castor oil, tallow, whale and fish oils, grease, lard, and mixtures thereof). The fatty acids also can be synthetically prepared (e.g., by the oxidation of petroleum, or by hydrogenation of carbon monoxide by the Fischer-Tropsch process). Resin acids are suitable such as rosin and those resin acids in tall oil. Naphthenic acids are also suitable. Sodium and potassium soaps can be made by direct saponification of the fats and oils or by the neutralization of the free fatty acids which are prepared in a separate manufacturing process. Particularly useful are the sodium and potassium salts of the mixtures of fatty acids, derived from coconut oil and tallow, i.e., sodium or potassium tallow and coconut soap.

Soaps and fatty acids also act as detergent builders in detergent compositions because they remove multivalent ions by precipitation.

Anionic surfactants also includes water-soluble salts, particularly the alkali metal salts of organic sulfuric reaction products having in their molecular structure an alkyl radical containing from about 8 to about 22 carbon atoms and a sulfonic acid or sulfuric acid ester radical. (Included in the term alkyl is the alkyl portion of higher acyl radicals.) Examples of this group of non-soap anionic surfactants which form a part of the preferred built detergent compositions of the present inventon are the sodium or potassium alkyl sulfates, especially those obtained by sulfating the higher alcohols ($C_8$–$C_{18}$ carbon atoms) produced by reducing the glycerides of tallow or coconut oil; sodium or potassium alkyl benzene sulfonates, in which the alkyl group contains from about 9 to about 15 carbon atoms, in straight chain or branched chain configuration, sodium alkyl glyceryl ether sulfonates, especially those ethers of higher alcohols derived from tallow and coconut oil; sodium coconut oil fatty acid monoglyceride sulfonates and sulfates; sodium or potassium salts of sulfuric acid esters of the reaction product of one mole of a higher fatty alcohol (e.g., tallow or coconut oil alcohols) and about 1 to 6 moles of ethylene oxide; sodium or potassium salts of alkyl phenol ethylene oxide ether sulfate with about 1 to about 10 units of ethylene oxide per molecule and in which the alkyl radicals contain about 8 to about 12 carbon atoms.

Additional examples of non-soap anionic surfactants which come within the terms of the present invention are the reaction product of fatty acids esterified with isothionic acid and neutralized with sodium hydroxide where, for example, the fatty acids are derived from coconut oil; sodium or potassium salts of fatty acid amide of methyl lauride in which the fatty acids, for example are derived from coconut oil.

Still other anionic surfactants include the class designated as succinamates. This class includes such surface active agents as disodium N-octadecylsulfo succinamate; tetrasodium N-(1,2-dicarboxyethyl)-N-octadecylsulfo-succinamate; the diamyl ester of sodium sulfosuccinic acid and the dihexyl ester of sodium sulfosuccinic acid; dioctyl ester of sodium sulfosuccinic acid.

Anionic phosphate surfactants are also useful in the present invention. These are surface active materials having substantial detergent capability in which the anionic solubilizing group connecting hydrophobic moieties is an oxy acid of phosphorus. The more common solubilizing groups, of course are —$SO_4H$, —$SO_3H$, and —$CO_2H$. Alkyl phosphate esters such as (R—O)$_2PO_2H$ and ROPO$_3H_2$ in which R represents an alkyl chain containing from about 8 to about 20 carbon atoms are useful.

These esters can be modified by including in the molecule from one to about 40 alkylene oxide units, e.g., ethylene oxide units.

Particularly useful anionic surfactants useful herein are alkyl ether sulfates. These materials have the formula RO($C_2H_4O$)$_x$SO$_3$M wherein R is alkyl or alkenyl of about 10 to about 20 carbon atoms, x is 1 to 30, and M is a salt-forming cation defined hereinbefore.

The alkyl ether sulfates are condensation products of ethylene oxide and monohydric alcohols having about 10 to about 20 carbon atoms. Preferably, R has 14 to 18 carbon atoms. The alcohols can be derived from fats, e.g., coconut oil or tallow, or can be synthetic. Such alsohols are reacted with 1 to 30, and especially 3 to 6, molar proportions of ethylene oxide and the resulting mixture of molecular species, having, for example, an average of 3 to 6 moles of ethylene oxide per mole of alcohol, is sulfated and neutralized.

Other suitable surfactants utilized herein are olefin and paraffin sulfonates having from about 12 to about 24 carbon atoms.

(B) Nonionic surfactants

Alkoxylated nonionic surfactants may be broadly defined as compounds produced by the condensation of alkylene oxide groups (hydrophilic in nature) with an organic hydrophobic compound, which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

Alkoxylated nonionic surfactants include:

(1) The condensation product of aliphatic alcohols having from 8 to 22 carbon atoms, in either straight chain or branched chain configuration, with from about 5 to about 20 moles of ethylene oxide per mole of alcohol.

(2) The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 5 to 25 moles of ethylene oxide per mole of alkyl phenol. The alkyl substituent in such compounds may be derived from polymerized propylene, diisobutylene, octene, or nonene, for example.

(3) Materials derived from the condensation of ethylene oxide with a product resulting from the reaction of propylene oxide and a compound with reactive hydrogen such as glycols and amines, for example, compounds containing from about 40% to about 80% polyoxyethylene by weight resulting from the reaction of ethylene oxide with a hydrophobic base constituted of the reaction product of ethylene diamine and propylene oxide.

Non-polar nonionic surfactants include the amine oxides and corresponding phosphine oxides. Useful amine oxide surfactants include those having the formula $R^1R^2R^3N\rightarrow O$ wherein $R^1$ is an alkyl group containing from about 10 to about 28 carbon atoms, from 0 to about 2 hydroxy groups and from 0 to about 5 ether linkages, there being at least one moiety of $R^1$ which is an alkyl group containing from about 10 to about 18 carbon atoms and 0 ether linkages, and each $R^2$ and $R^3$ are selected from the group consisting of alkyl radicals and hydroxyalkyl radicals containing from 1 to about 3 carbon atoms;

Specific examples of amine oxide surfactants include: dimethyldodecylamine oxide, dimethyltetradecylamine oxide, ethylmethyltetradecylamine oxide, cetyldimethylamine oxide, diethyltetradecylamine oxide, dipropyldodecylamine oxide, bis-(2-hydroxyethyl)-dodecylamine oxide, bis-(2-hydroxypropyl)methyltetradecylamine oxide, dimethyl-(2-hydroxydodecyl)amine oxide, and the corresponding decyl, hexadecyl and octadecyl homologs of the above compounds.

(C) Zwitterionic Surfactants

Zwitterionic surfactants include derivatives of aliphatic quaternary ammonium, phosphonium, and sulfonium compounds in which the aliphatic moiety can be straight or branched chain and wherein one of the aliphatic substitutents contains from about 8 to 24 carbon atoms and one contains an anionic water-solubilizing group. Particularly preferred zwitterionic materials are the ethoxylated ammonium sulfonates and sulfates disclosed in U.S. Pat. No. 3,925,262, Laughlin et al, issued Dec. 9, 1975 and 3,929,678, Laughlin et al, issued Dec. 30, 1975, said patents being incorporated herein by reference.

(D) Ampholytic Surfactants

Ampholytic surfactants include derivatives of aliphatic heterocyclic secondary and ternary amines in which the aliphatic moiety can be straight chain or branched and wherein one of the aliphatic substitutents contains from about 8 to about 24 carbon atoms and at least one aliphatic substituent contains an anionic water-solubilizing group.

(E) Cationic Surfactants

Cationic surfactants comprise a wide variety of compounds characterized by one or more organic hydrophobic groups in the cation and generally by a quaternary nitrogen associated with acid radical. Pentavalent nitrogen ring compounds are also considered quaternary nitrogen compounds. Suitable anions are halides, methyl sulfate and hydroxide. Tertiary amines can have characteristics similar to cationic surfactants at washing solutions pH values less than about 8.5.

A more complete disclosure of cationic surfactants can be found in U.S. Pat. No. 4,228,044 by Cushman M. Cambre for Laundry Detergent Composition Having Enhanced Particulate Soil Removal and Antiredeposition Performance, issued Oct. 14, 1980, said patent being incorporated herein by reference.

When cationic surfactants are used in combination with anionic surfactants and certain detergency builders including polycarboxylates, compatibility must be considered. A type of cationic surfactant generally compatible with anionic surfactants and polycarboxylates is a $C_{8-18}$ alkyl tri $C_{1-3}$ alkyl ammonium chloride or methyl sulfate.

For a more complete disclosure of surfactants which are suitable for incorporation in detergent compositions, one can consult U.S. Pat. No. 4,056,481, Tate (Nov. 1, 1977); 4,049,586, Collier (Sept. 20, 1977); 4,040,988, Vincent et al (Aug. 9, 1977); 4,035,257, Cherney (July 12, 1977); 4,033,718, Holcolm et al (July 5, 1977); 4,019,999, Ohren et al (Apr. 26, 1977); 4,019,998, Vincent et al (Apr. 26, 1977); and 3,985,669, Krummel et al (Oct. 12, 1976); all of said patents being incorporated herein by reference.

Optional Detergency Builders

The detergent compositions of the present invention can contain detergency builders in addition to the novel sequestering agent compounds described herein.

Suitable additional polycarboxylate detergency builders include the acid form and alkali metal, ammonium and substituted ammonium salts of citric, ascorbic, phytic, mellitic, benzene pentacarboxylic, oxydiacetic, carboxymethyloxysuccinic, carboxymethyloxymalonic, cis-cyclohexanehexacarboxylic, cis-cyclopentanetetracarboxylic and oxydisuccinic acids. Also suitable are the polymeric polycarboxylate materials described in U.S. Pat. No. 3,364,103 and polycarboxylate polymers and copolymers described in U.S. Pat. No. 3,308,067, Diehl, issued Mar. 7, 1967, both patents incorporated herein by reference.

With due regard to their stability in aqueous media, the polyacetal carboxylates disclosed in U.S. Pat. No. 4,144,226 issued Mar. 13, 1979, to Crutchfield et al and U.S. Pat. No. 4,146,495 issued Mar. 27, 1979 to Crutchfield et al can be incorporated in the compositions of the invention.

Additional suitable polycarboxylates are those containing nitrogen such as ethylenediaminetetraacetic acid, diethylenetriaminepentaacetic acid, hydroxyethyl ethylenediamine triacetic acid and nitrilotriacetic acid and alkali metal, ammonium and substituted ammonium salts thereof.

Polyphosphonate detergency builders comprise a large range of organic compounds having two or more

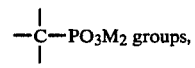

wherein M is a hydrogen or a salt-forming radical. Suitable phosphonates include ethane-1-hydroxy-1,1-diphosphonates, ethanehydroxy-1,1,2-triphosphonates and their oligomeric ester chain condensates. Suitable polyphosphonates for use in the compositions of the invention also include nitrogen-containing polyphosphonates such as ethylenediaminetetramethylene phosphonic acid and diethylenetriaminepentamethylene phosphonic acid and alkali metal, ammonium and substituted ammonium salts thereof. In common with other phosphorus-containing components, the incorporation of phosphonates may be restricted or prohibited by government regulation.

As discussed hereinbefore $C_{8-24}$ alkyl monocarboxylic acid and soluble salts thereof have a detergent builder function in addition to surfactant characteristics.

Inorganic detergency builders useful in the compositions of the invention at total combined levels of from 0% to about 75% by weight, include alkali metal phosphates, sodium aluminosilicates, alkali metal silicates and alkali metal carbonates.

Granular laundry detergent compositions generally contain at least about 40% of inorganic salts and it is desirable that a major portion of such salts have a contribution to the detergent effect. Inorganic detergency builders are less useful in liquid detergent compositions of the invention and can be omitted to provide optimum physical properties and optimum levels of the essential components.

Phosphate detergency builders include alkali metal orthophosphates which remove multivalent metal cations from laundry solutions by precipitation and the polyphosphates such as pyrophosphates, tripolyphosphates and water-soluble metaphosphates that sequester multivalent metal cations in the form of soluble complex salts. Alkali metal polyphosphates in anhydrous form have the general formula $M_{n+2}P_nO_{3n+1}$ wherein M is sodium or potassium and n is at least 1. Sodium pyrophosphate and sodium tripolyphosphate are particularly suitable in granular detergent compositions and potassium pyrophosphate is suitable in liquid detergent compositions to the extent that governmental regulations do not restrict or prohibit the use of phosphorus-containing compounds in detergent compositions.

Crystalline aluminosilicate ion exchange materials useful in the practice of this invention have the formula $Na_z[(AlO_2)_z.(SiO_2)]xH_2O$ wherein z and y are at least about 6, the molar ratio of z to y is from about 1.0 to about 0.5 and x is from about 10 to about 264. In a preferred embodiment the aluminosilicate ion exchange material has the formula $Na_{12}[(AlO_2)_{12}(SiO_2)_{12}]xH_2O$ wherein x is from about 20 to about 30, especially about 27.

Amorphous hydrated aluminosilicate material useful herein has the empirical formula: $Na_z(zAlO_2.ySiO_2)$, z is from about 0.5 to about 2, y is 1 and said material has a magnesium ion exchange capacity of at least about 50 milligram equivalents of $CaCO_3$ hardness per gram of anhydrous aluminosilicate.

The aluminosilicate ion exchange builder materials herein are in hydrated form and contain from about 10% to about 28% of water by weight if crystalline and potentially even higher amounts of water if amorphous. Highly preferred crystalline aluminosilicate ion exchange materials contain from about 18% to about 22% water in their crystal matrix. The crystalline aluminosilicate ion exchange materials are further characterized by a particle size diameter of from about 0.1 micron to about 10 microns. Amorphous materials are often smaller, e.g., down to less than about 0.01 micron. Preferred ion exchange materials have a particle size diameter of from about 0.2 micron to about 4 microns. The term "particle size diameter" herein represents the average particle size diameter of a given ion exchange material as determined by conventional analytical techniques such as, for example, microscopic determination utilizing a scanning electron microscope. The crystalline aluminosilicate ion exchange materials herein are usually further characterized by their calcium ion exchange capacity, which is at least about 200 mg. equivalent of $CaCo_3$ water hardness/gm. of aluminosilicate, calculated on an anhydrous basis, and which generally is in the range of from about 300 mg.eq./g. to about 352 mg. eq./g. The aluminosilicate ion exchange materials herein are still further characterized by their calcium ion exchange rate which is at least about 2 grains Ca.++/gallon/minute/gram of aluminosilicate (anhydrous basis), and generally lies within the range of from about 2 grains/gallons/minute/gram to about 6 grains/gallons/minute/gram, based on calcium ion hardness. Optimum aluminosilicate for builder purposes exhibit a calcium ion exchange rate of at least about 4 grains/gallons/minute/gram.

The amorphous aluminosilicate ion exchange materials usually have a Mg++ exchange capacity of at least about 50 mg. eq. $CaCO_3/g$ (12 mg. Mg++/g.) and a Mg++ exchange rate of at least about 1 gr./gal./min./g./gal. Amorphous materials do not exhibit an observable diffraction pattern when examined by Cu radiation (1.54 Angstrom Units).

Aluminosilicate ion exchange materials useful in the practice of this invention are commercially avilable. The aluminosilicates useful in this invention can be crystalline or amorphous in structure and can be naturally-occurring aluminosilicates or synthetically derived. A method for producing aluminosilicate ion exchange materials is discussed in U.S. Pat. No. 3,985,669, issued Oct. 12, 1976, incorporated herein by reference. Preferred synthetic crystalline aluminosilicate ion exchange materials useful herein are available under the designation Zeolite A, Zeolite B, and Zeolite X.

Suitable alkali metal silicates have a mole ratio of $SiO_2$:alkali metal oxide in the range of from about 1:1 to about 4:1. The alkali metal silicate suitable herein include commercial preparations of the combination of silicon dioxide and alkali metal oxide or carbonate fused together in varying proportions according to, for example, the following reaction:

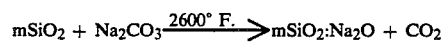

$$mSiO_2 + Na_2CO_3 \xrightarrow{2600° F.} mSiO_2:Na_2O + CO_2$$

The value of m, designating the molar ratio of $SiO_2$:$Na_2O$, ranges from about 0.5 to about 4 depending on the proposed use of the sodium silicate. The term "alkali metal silicate" as used herein refers to silicate solids with any ratio of $SiO_2$ to alkali metal oxide. Silicate solids normally possess a high alkalinity content; in addition water of hydration is frequently present as, for example, in metasilicates which can exist having 5, 6, or 9 molecules of water. Sodium silicate solids with a $SiO_2$:$Na_2O$ mole ratio of from about 1.5 to about 3.5, are preferred in granular laundry detergent compositions.

Silicate solids are frequently added to granular detergent compositions as corrosion inhibitors to provide protection to the metal parts of the washing machine in which the detergent composition is utilized. Silicates have also been used to provide a degree of crispness and pourability to detergent granules which is very desirable to avoid lumping and caking.

Alkali metal carbonates are useful in the granular compositions of the invention as a source of washing solution alkalinity and because of the ability of the carbonate ion to remove calcium and magnesium ions from washing solutions by precipitation.

Preferred granular compositions free of inorganic phosphates contain from about 10% to about 40% sodium carbonate, from 0% to about 30% sodium aluminosilicate, from about 0.5% to about 4% sodium silicate solids, from about 10% to about 35% of the ether carboxylates of the invention and from abourt 10% to about 25% surfactant.

Preferred liquid compositions free of inorganic phosphates have a pH of from about 6 to about 8.5 in 1% water solution and contain from about 10% to about 20% non-soap surfactants, from about 8% to about 20% by weight of $C_{12-18}$ alkylmonocarboxylic acids such as palm, palm kernel and coconut fatty acids and oleic, myristic and lauric acids and from about 2% to about 20% of the ether polycarboxylate sequestering agents of the invention.

Additional Optional Components

Granular compositions of this invention can contain materials such as sulfates, borates, perborates and water of hydration.

Liquid compositions of this invention can contain water and other solvents. Low molecular weight primary or secondary alcohol exemplified by methanol, ethanol, propanol, and isopropanol are suitable. Monohydric alcohols are preferred for solubilizing the surfactant but polyols containing from 2 to about 6 carbon atoms and from 2 to about 6 hydroxy groups can be used and can provide improved enzyme stability. Examples of polyols include propylene glycol, ethylene glycol, glycerine and 1,2-propanediol. Ethanol is a particularly preferred alcohol.

The compositions of the invention can contain such materials as proteolytic and amylolytic enzymes, fabric whiteners and brighteners, sudsing control agents, hydrotropes such as sodium toluene or xylene sulfonate, perfumes, colorants, opacifiers, anti-redeposition agents and alkalinity control or buffering agents such as monoethanolamine and triethanolamine. The use of these materials is known in the detergent art.

Materials that provide clay soil removal/anti-redeposition benefits can also be incorporated in the detergent compositions of the invention and are particularly useful in liquid compositions of the invention.

These clay soil removal/anti-deposition agents are usually included at from about 0.1 to about 10% by weight of the composition.

One group of preferred clay soil removal/anti-redeposition agents are the ethoxylated amines disclosed in European patent application No. 112,593 to James M. Vander Meer, published July 4, 1984, herein incorporated by reference. Another group of preferred clay soil removal/anti-redeposition agents are the cationic compounds disclosed in European patent application No. 111,965 to Young S. Oh and Eugene P. Gosselink, published June 27, 1984, herein incorporated by reference. Other clay soil removal/anti-redeposition agents which can be used include the ethoxylated amine polymers disclosed in European patent application No. 111,984 to Eugene P. Gosselink, published June 27, 1984; the zwitterionic compounds disclosed in European patent application No. 111,976 to Donn N. Rubingh and Eugene P. Gosselink, published June 27, 1984; the zwitterionic polymers disclosed in European patent application No. 112,592 to Eugene P. Gosselink, published July 4, 1984; and the amine oxides disclosed in U.S. application Ser. No. 516,612 to Daniel S. Connor, filed July 22, 1983, all of which are incorporated by reference.

In a preferred embodiment, the detergent compositions of the invention comprise from about 1% to about 8% of an effective particulate dispersant such as the polyacrylates and polyacrylatemaleic acid or anhydride copolymers with an average molecular weight of from about 3000 to about 15,000. Aminocarboxylates and aminophosphates such as diethylenetriaminepentaacetates and diethylenetriaminepentamethylenephosphonates at levels of from about 0.2% to about 3% are useful as heavy metal ion chelants, particularly in combination with particulate dispersants.

The following embodiments illustrate, but are not limiting of, detergent compositions of the present invention:

EXAMPLE 1

| Component | Wt. % |
|---|---|
| Sodium $C_{14}$–$C_{15}$ alkylethoxysulfate | 10.7 |
| $C_{13}$ linear alkyl benzene sulfonic acid | 4.3 |
| $C_{12}$–$C_{14}$ alkylpolyethoxylate (6) | 0.5 |
| Sodium toluene sulfonate | 1.0 |
| Tetrasodium 3,3-dicarboxy-4-oxa-1,6-hexanedioate | 32.9 |
| Sodium carbonate | 20.3 |
| Sodium silicate | 5.8 |
| Minors and water | Balance to 100 |

The components are added together with continuous mixing to form an aqueous slurry which is then spray dried to form the composition.

EXAMPLE II

A liquid detergent composition is as follows:

| Component | Wt. % |
|---|---|
| Sodium $C_{14}$–$C_{15}$ alkyl polyethoxy (2.5) sulfate | 8.3 |
| $C_{12}$–$C_{14}$ alkyl dimethyl amine oxide | 3.3 |
| Potassium toluene sulfonate | 5.0 |
| Monoethanolamine | 2.3 |
| Tetrapotassium 3,3-dicarboxy-4-oxa-1,6-hexanedioate | 18.2 |
| Minors and water | Balance to 100 |

The components are added together with continuous mixing to form the composition.

EXAMPLES III and IV

Liquid detergent compositions are as follows:

| Component | Wt. % III | Wt. % IV |
|---|---|---|
| $C_{14}$–$C_{15}$ alkylpolyethoxy (2.25) sulfuric acid | 12.0 | 10.8 |
| $C_{13}$ linear alkylbenzene sulfonic acid | 8.0 | 8.0 |
| $C_{12}$ alkyl trimethylammonium chloride | 0.6 | 1.2 |
| $C_{12}$–$C_{13}$ alcohol polyethoxylate (6.5) | 5.0 | 6.5 |
| Coconut fatty acid | 10.0 | 13.0 |
| Oleic acid | 0.5 | 2.0 |
| 3,3-dicarboxy-4-oxa-1,6-hexanedioic acid | 4.0 | 5.0 |
| Citric acid monohydrate | 2.0 | 0.2 |
| Diethylenetriamine pentaacetic acid | 0.2 | 0.2 |
| Protease enzyme | 0.8 | 0.8 |
| Amylase enzyme | 0.2 | 0.2 |
| Monoethanolamine | 2.0 | 2.0 |
| Sodium hydroxide | 2.4 | 1.7 |
| Potassium hydroxide | 1.1 | 2.7 |
| 1,2-Propanediol | 3.5 | 7.3 |
| Ethanol | 8.5 | 7.8 |
| Formic acid | 0.08 | 0.7 |
| Boric acid | 1.3 | |
| Calcium ion | 0.03 | 0.03 |

| | Wt. % | |
|---|---|---|
| Component | III | IV |
| Minors and water | Balance to 100 | |

Examples III and IV are prepared by adding the components together with continuous mixing and adjustment of pH to 8.1.

The compositions of Examples I through IV provide excellent performance as laundry detergents.

In Examples I through IV, oxacyclohexane-2,2,3,6-tetracarboxylic acid or its sodium salt and oxacyclopentane-2,2,3,5-tetracarboxylic acid or its sodium salt are substituted respectively for 3,3-dicarboxy-4-oxa-1,6-hexanedioic acid or its sodium salt. Substantially equivalent results are obtained.

The following compounds are substituted for 3,3-dicarboxy-4-oxa-1,6-hexanedioic acid or the sodium salt thereof in Example I through IV:

3,3-dicarboxy-4-oxa-5-hydroxy-1,6-hexanedioic acid or the sodium salt thereof.

3,3,5-tricarboxy-4-oxa-1,6-hexanedioic acid or the sodium salt thereof.

3,3,5-tricarboxy-4-oxa-5-hydroxymethyl-1,6-hexanedioic acid or the sodium salt thereof.

Substantially equivalent results are obtained.

What is claimed is:

1. Metal sequestering agent compounds represented by the chemical structure

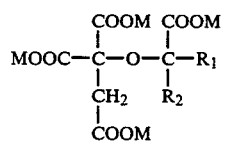

wherein M is hydrogen or a cation wherein the resultant salt is water-soluble and R₁ and R₂ can be the same or different and are selected from the group consisting of H, CH₃, CH₃CH₂, OH, CH₂OH, CH₂CH₂OH, COOM, CH₂COOM, and CH₂CH₂COOM, M having the same meaning as above.

2. A compound according to claim 1 wherein R₁ and R₂ are hydrogen.

3. A compound according to claim 2 wherein M is sodium.

4. A detergent composition comprising from about 0.5% to about 98% by weight of a surfactant and from about 2% to about 99.5% by weight of a metal sequestering agent compound represented by the chemical structure

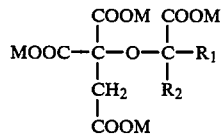

wherein M is hydrogen or a cation wherein the resultant salt is water-soluble and R₁ and R₂ can be the same or different and are selected from the group consisting of H, CH₃, CH₃CH₂, OH, CH₂OH, CH₂CH₂OH, COOM, CH₂COOM, and CH₂CH₂COOM, M having the same meaning as above.

5. The composition of claim 4 which comprises from about 5% to about 30% by weight of a surfactant and from about 4% to about 50% by weight of said metal sequestering agent compound.

6. The composition of claim 4 in granular form which comprises from about 10 to about 25% by weight of a surfactant and from about 10% to about 35% by weight of said metal sequestering agent compounds wherein R₁ and R₂ are hydrogen and M is sodium.

7. The composition of claim 4 in liquid form which comprises from about 10% to about 20% by weight of non-soap surfactants, from about 8% to about 20% by weight of C₁₂–C₁₈ monocarboxylic acids and from about 2% to about 25% by weight of said metal sequestering agent compound wherein R₁ and R₂ are hydrogen.

8. A method of making compounds represented by the formula

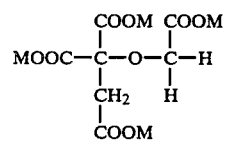

wherein M is alkali metal and acids thereof, which comprises reacting 1,3-butadiene with a compound represented by the formula

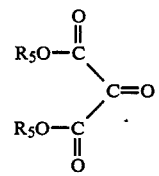

wherein R₅ is methyl or ethyl to yield

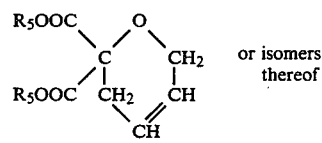

or isomers thereof which is reacted with an alkali metal hydroxide to yield

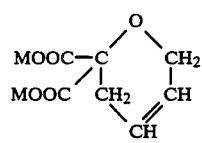

which is oxidized and neutralized to yield

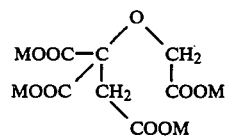

or hydrates thereof.

* * * * *